(12) United States Patent
Griffin et al.

(10) Patent No.: US 8,799,014 B2
(45) Date of Patent: Aug. 5, 2014

(54) SCREENING INTEREST MANAGER

(75) Inventors: Sara J. Griffin, Lee's Summit, MO (US); Sara J. Boswell, Blue Springs, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 413 days.

(21) Appl. No.: 12/982,699

(22) Filed: Dec. 30, 2010

(65) Prior Publication Data
US 2011/0166874 A1 Jul. 7, 2011

Related U.S. Application Data

(60) Provisional application No. 61/291,720, filed on Dec. 31, 2009.

(51) Int. Cl.
*G06Q 50/00* (2012.01)

(52) U.S. Cl.
USPC .................................................. 705/2; 705/3

(58) Field of Classification Search
USPC .......................................................... 705/2
See application file for complete search history.

(56) References Cited

U.S. PATENT DOCUMENTS

| | | | |
|---|---|---|---|
| 6,194,217 B1 * | 2/2001 | Matson | 436/63 |
| 7,698,154 B2 * | 4/2010 | Marchosky | 705/3 |
| 2006/0190303 A1 * | 8/2006 | Yourist et al. | 705/3 |

* cited by examiner

*Primary Examiner* — Hiep V Nguyen
(74) *Attorney, Agent, or Firm* — Shook, Hardy & Bacon L.L.P.

(57) ABSTRACT

Methods, systems, and computer storage media are provided for managing the availability of health record data of a pool of individuals by use of default rules and authorizations.

20 Claims, 8 Drawing Sheets

SCREENING INTEREST MANAGER

This application claims the benefit of U.S. Provisional Application Ser. No. 61/291,720, filed Dec. 31, 2009, which is hereby incorporated by reference in its entirety.

BACKGROUND

The accessibility of health-related data from a sizable portion of the general population is essential for effective medical research that can benefit society at large. In particular, applied research (e.g., clinical trials) and translational research depend greatly on access to vast amounts of health-related data from general or specific segments of the population.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to a mechanism for managing the availability of health record data of a pool of individuals. In embodiments, default rules and authorizations are utilized to generate classifications for individuals as screening eligible or screening not eligible. The classifications govern whether health data from person-centric health records is available for screening (also known as "pre-screening") in order to identify individuals that may qualify for involvement in research activities (e.g., clinical trials, research studies) or registries.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide for systems, methods, and computer storage media for managing the availability of health record data of a pool of individuals by, among other things, use of default rules and authorizations.

Having briefly described embodiments of the present invention, an exemplary operating environment suitable for use in implementing embodiments of the present invention is described below. Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

Figure 1:
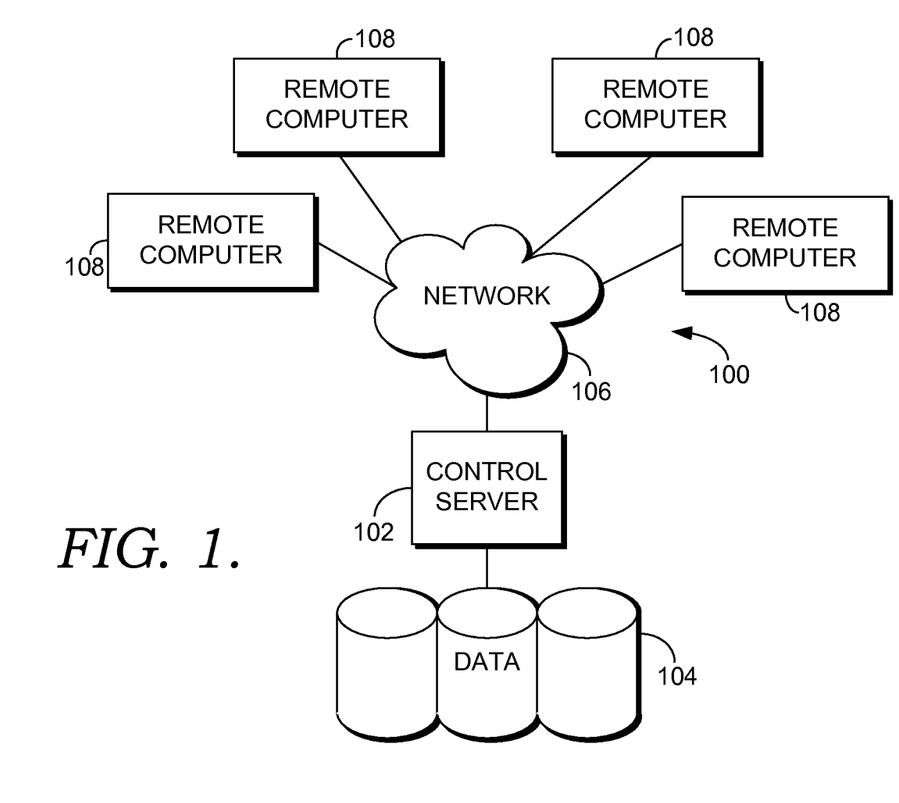
FIG. 1 is a block diagram of an exemplary computing environment suitable for use in implementing the present invention.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer-readable media, for instance, database cluster 104. Computer-readable media can be any available media that may be accessed by server 102, and includes volatile and nonvolatile media, as well as removable and non-removable media. By way of example, and not limitation, computer-readable media may include computer storage media and communication media. Computer storage media may include, without limitation, volatile and nonvolatile media, as well as removable and nonremovable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home healthcare environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in nontraditional medical care environments so that the entire healthcare community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

As previously mentioned, embodiments of the invention relate to a mechanism for managing the availability of health record data of a pool of individuals. Patient health record data resides at least in person-centric electronic medical or health records, such that each individual of a pool of individuals has such a health record. The term "health record" or "chart" is not meant to be limited to any particular type of unified record that stores health data for an individual, examples of which include an electronic medical record (EMR), electronic health record (EHR), personal health record (PHR), continuity of care record (CCR), among others, or any portion thereof, such as a medication administration record (MAR or eMAR). Furthermore, the terms "patient", "individual", "participant" and "person" may be used interchangeably herein to refer to someone who has an associated medical or health record.

In embodiments, categorizing specific individuals as "screening eligible" or "screening not eligible" is achieved by the utilization of default rules and authorizations. Additionally, institutional or organizational rules may also be applied in the categorization process. Once categorizations are established, health data from the person-centric health records of individuals in the "screening eligible" category may selectively be made accessible for purposes of evaluating the potential eligibility of such individuals for research activities or registries. In another aspect, the categorization of individuals as "screening eligible" or "screening not eligible" may be further extended to contemplate particular types of research activities or registries. Accordingly, further authorizations are received from the individuals related to such particular types of research activities or registries. It should also be understood that the term screening is not meant to be limited to a particular type of medical or medical research related screening, examples of which include feasibility screening, test screening, or any other type of medical screening or pre-screening.

Figure 2:
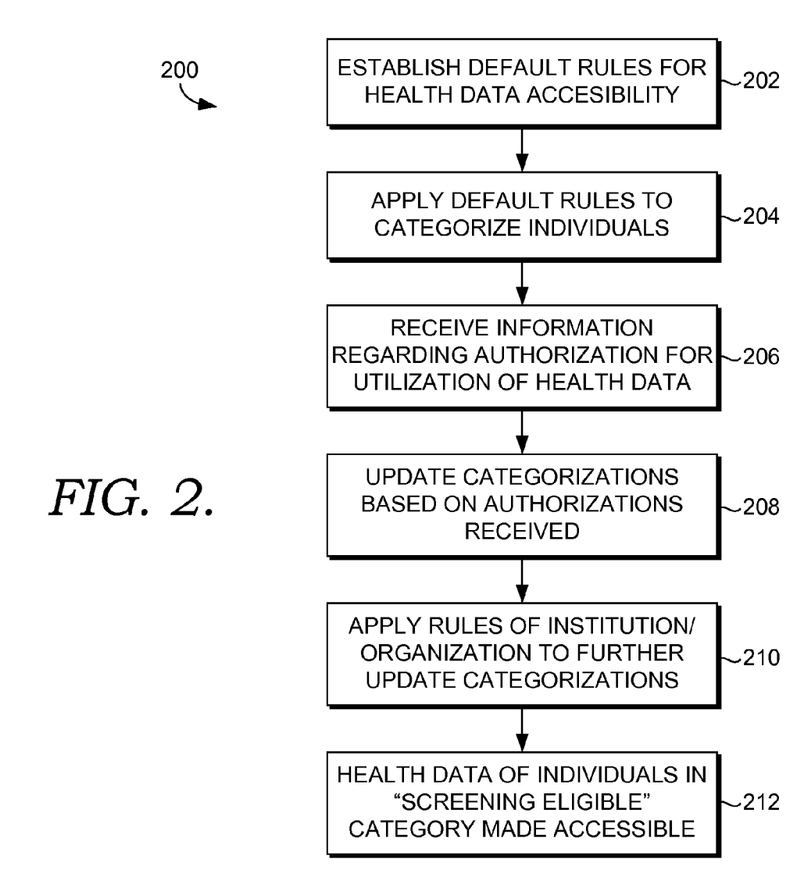
FIG. 2 is a flow diagram illustrating a method for managing the availability of heath record data of a pool of individuals, in accordance with an embodiment of the present invention.

With reference to FIG. 2, a method 200 is provided for managing the availability of health record data of a pool of individuals. According to the method 200, one or more default rules are established 202 regarding the accessibility of health data from person-centric health records of the pool of individuals, the accessibility being for purposes of evaluating the potential eligibility of such individuals for research activities or registries. The default rules may serve as a baseline filter for establishing a preliminary approach to person-specific health data availability. For instance, an institution or health organization may set a default rule to initially consider health data from the person-centric health records of all individuals in a given pool (subject to being overridden by other rules or regulations) as being available for purposes of evaluating the potential eligibility of such individuals for research activities or registries ("available rule"). Alternatively, another default rule may initially exclude all individuals in the pool from qualifying to having their health data considered available for such purposes ("not available rule").

The default rules, in step 204, are then applied to categorize individuals of the pool of individuals as "screening eligible" or "screening not eligible." For at least some of the person-centric health records for the pool of individuals, in step 206, information regarding authorizations given by such individuals for utilization of their specific health data in evaluating the potential eligibility of the individual for research activities or registries is received and stored. The authorizations, in one aspect, constitute indications from the respective individuals as to the individual's desire to have their specific health data utilized for the eligibility evaluation or screening. The authorization information may be directly inputted into the person-centric health record, or may be extracted from another data store and imported into the health record, as one example.

Thereafter, in step 208, based on the authorizations received, the categorizations for the pool of individuals are appropriately updated as "screening eligible" or "screening not eligible" for each applicable individual. As one example, if the default rule applied was "available rule", then the "screening eligible" category would include all of the pool of individuals except for those who indicated they did not want their specific health data utilized for the eligibility evaluation or screening with respect to research activities or registries. In another example, if the default rule applied was "not available rule", then the "screening eligible" category would exclude all of the pool of individuals except for those who indicated they did in fact want their specific health data utilized for the eligibility evaluation or screening with respect to research activities or registries. As one option, in step 210, a set of rules established by a health institution or organization may be applied to further update the categorization of individuals of the pool of individuals as "screening eligible" or "screening not eligible." For instance, a rule may be applied to ensure that individuals from the pool of individuals having a certain type of disease or condition (according to data in their respective health record) are automatically categorized as "screening not eligible", regardless of standard default rules or authorizations received from applicable individuals. The health data from person-centric health records of individuals in the "screening eligible" category, in step 212, is made accessible for eligibility evaluation or screening with respect to research activities or registries. For instance, in one embodiment, if a research organization sought approval from a health organization to screen for patients of that health organization having a particular medical condition, the health data of those patients in the "screening eligible" category could be exposed for the limited purposes of discerning whether those individuals met certain criteria to qualify for a particular research activity (or registry).

Figure 3:
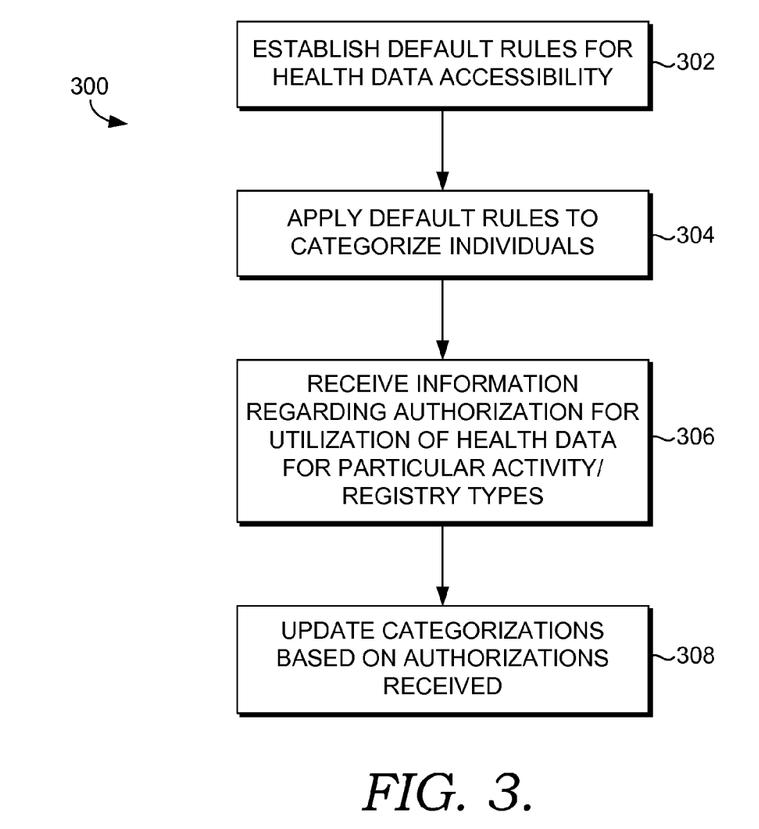
FIG. 3 is a flow diagram illustrating another method for managing the availability of heath record data of a pool of individuals, in accordance with an embodiment of the present invention.

With reference to FIG. 3, another method 300 is provided for managing the availability of health record data of a pool of individuals. Method 300 shares a number of steps with method 200. However, method 300 employs specific rules for categorizing individuals as "screening eligible" based on the particular type of research activity or registry for which such eligibility is to be determined. According to the method 300, one or more default rules are established 302 regarding the accessibility of health data from person-centric health records of the pool of individuals, the accessibility being for purposes of evaluating the potential eligibility of such individuals for research activities or registries. Default rules are then applied in step 304 to categorize individuals of the pool of individuals as "screening eligible" or "screening not eligible."

For at least some of the person-centric health records for the pool of individuals, in step 306, rules are invoked to prompt the associated individuals to indicate their authorization for utilization of their specific health data in evaluating the potential eligibility of the individual for one or more particular types of research activities or registries (and optionally their general authorization, as with step 206 of method 200), with such information regarding the authorization being received and stored. For instance, an individual may be prompted to indicate their authorization for screening their health data for potential eligibility in a clinical trial related to an experimental cancer treatment drug, or for a bone marrow registry, as examples.

Thereafter, in step 308, based on the authorizations received, the categorizations for the pool of individuals are appropriately updated as "screening eligible" or "screening not eligible" Institutional or organizational rules may also be applied to further update the categorization for the pool of individuals, followed by making the health data of individuals in the "screening eligible" category accessible for eligibility evaluation or screening with respect to research activities or registries.

Figure 4:
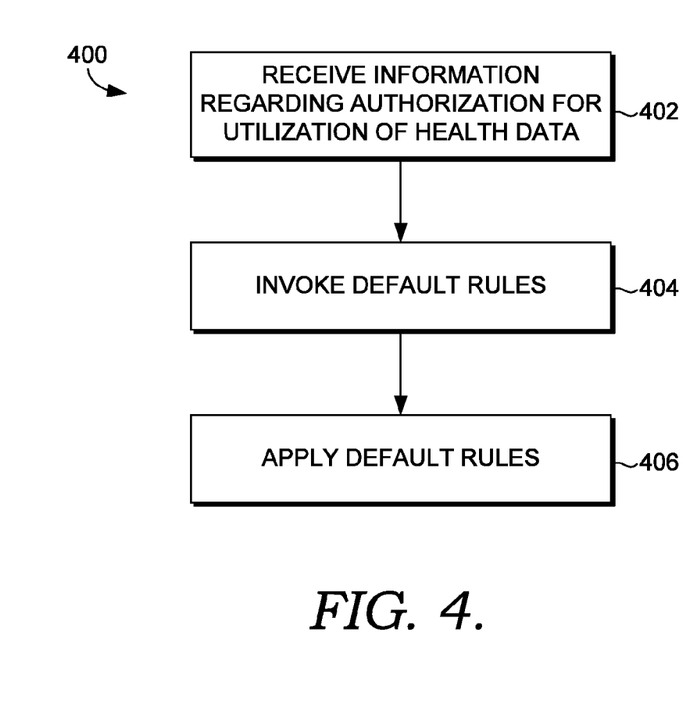
FIG. 4 is a flow diagram illustrating yet another method for managing the availability of heath record data of a pool of individuals, in accordance with an embodiment of the present invention.

With reference to FIG. 4, another method 400 is provided for managing the availability of health record data of a pool of individuals. Method 400 shares a number of steps with method 200. According to the method 400, information regarding authorizations given by individuals of a pool of individuals for utilization of their specific health data from person-centric health records to evaluate the potential eligibility of each individual for research activities or registries is received and stored, in step 402. One or more default rules are invoked, in step 404, regarding the accessibility of health data from the person-centric health records of the pool of individuals, the accessibility being for purposes of evaluating the potential eligibility of such individuals for research activities or registries. Based on the information received from the individuals regarding their authorizations (from step 402) and the application of the default rules (from step 404), such individuals are categorized as "screening eligible" or "screening not eligible", in step 406. Institutional or organizational rules may also be applied to further update the categorization for the pool of individuals, followed by making the health data of individuals in the "screening eligible" category accessible for eligibility evaluation or screening with respect to research activities or registries.

Figure 5:
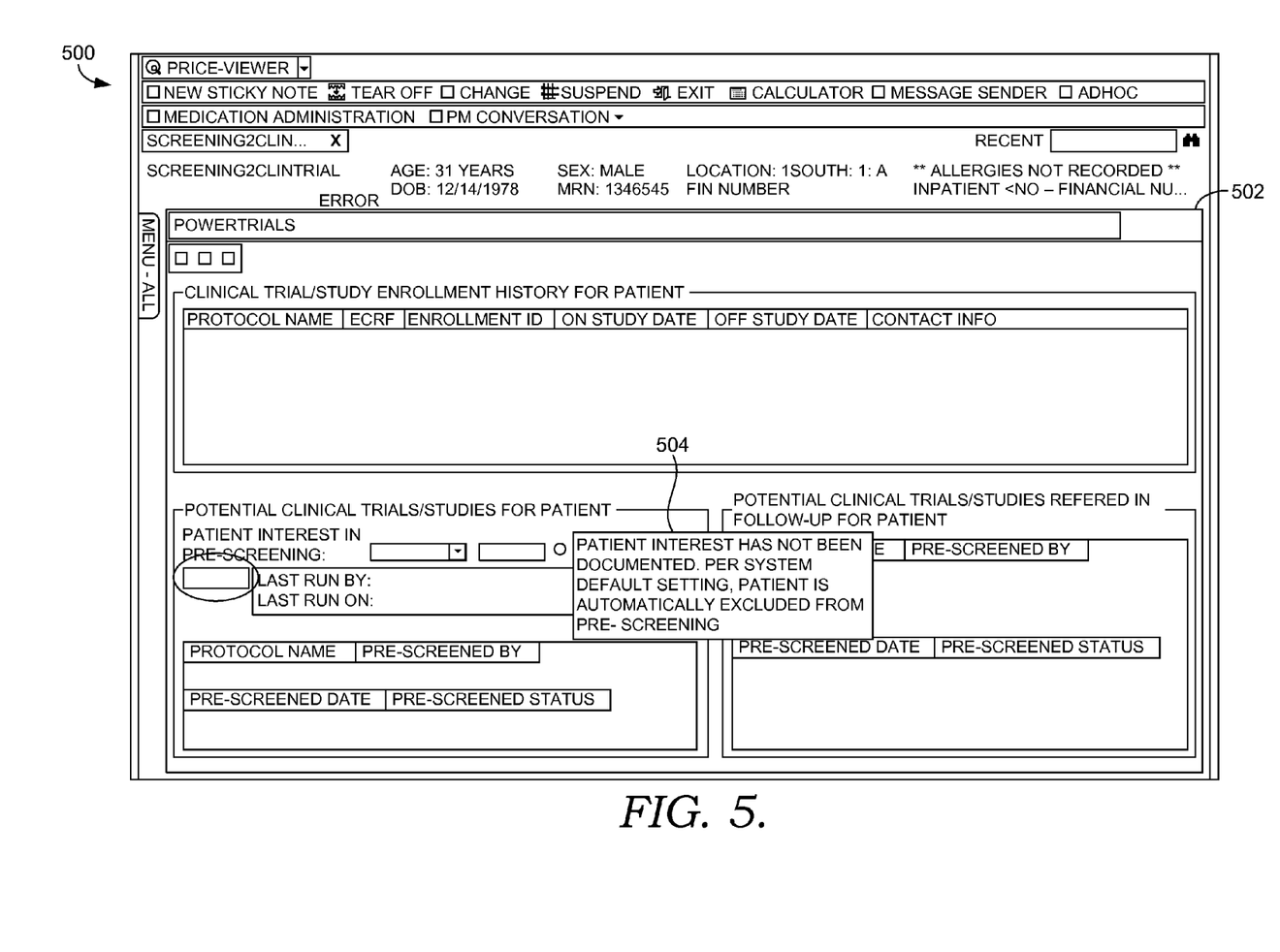
FIG. 5 is a screenshot illustrating an exemplary view of information regarding a particular patient's involvement in clinical research, with a default rule of "not available" for pre-screening applied.

Turning now to FIG. 5, an exemplary view 500 is provided of a clinical research activity manager 502 organizing information regarding a particular patient's involvement in clinical research. View 500 may be, for instance, integrated within the context of a particular patient's electronic health record view. The clinical research activity manager 502, in an embodiment, provides (a) clinical trial/study enrollment history for the specific patient, including protocol information and other trial/study details, (b) potential clinical trials/studies for the particular patient, as well as (c) any potential clinical trials/studies referred in follow-up for the patient. In view 500, the clinical research activity manager 502 is operating under the default rule of "not available" for pre-screening (described herein with respect to method 200, FIG. 2). Specifically, the particular patient record shows, via a pop-up window 504, the associated patient has not indicated an interest regarding (i.e., has not authorized) utilization of their specific health data in evaluating the potential eligibility of the individual for research activities or registries. Therefore, because of the default rule in effect, no option is provided in view 500 for selection of any particular protocols for which the associated patent could be pre-screened and the patient is classified as "screening not eligible".

Figure 6:
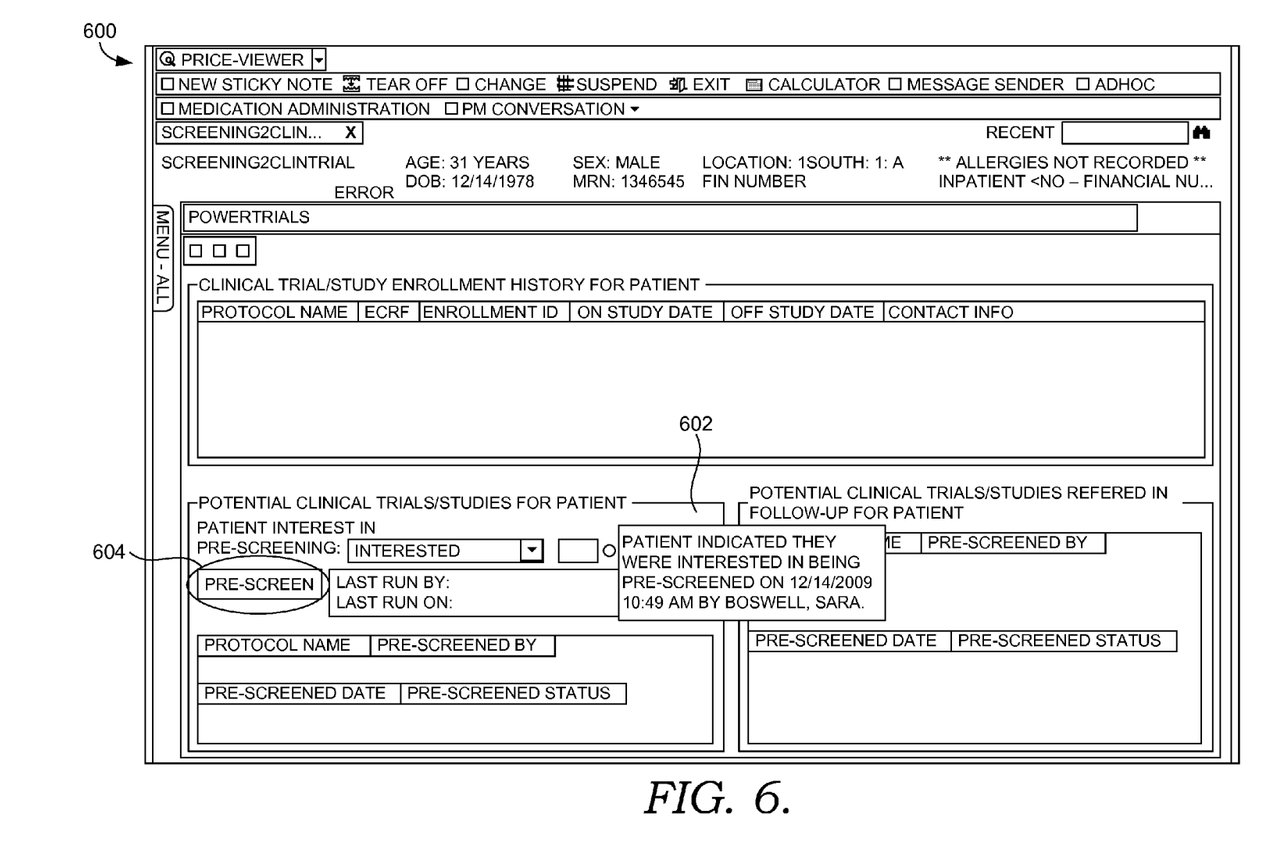
FIG. 6 is a screenshot illustrating another exemplary view of information regarding a particular patient's involvement in clinical research, with a default rule of "not available" for pre-screening applied.

FIG. 6 provides another exemplary view 600 of a clinical research activity manager, similar to view 500 of FIG. 5. In view 600, the default rule of "not available" for pre-screening is in effect. However, the particular patient record indicates, via a pop-up window 602, that patient has in fact indicated an interest in being eligible for pre-screening with respect to protocols that could apply for them. Accordingly, a pre-screen option 604 is presented and the patient is now classified as "screening eligible". This categorization as eligible may be, for instance, related to a specific clinical trial or study, or may be related to overall eligibility to have their health data reviewed for the limited purpose of determining their suitability for a range of research activities or registries. The clinician can select the pre-screen option 604, whereby the patient can be pre-screened to determine if they would qualify for any particular protocols.

Figure 7:
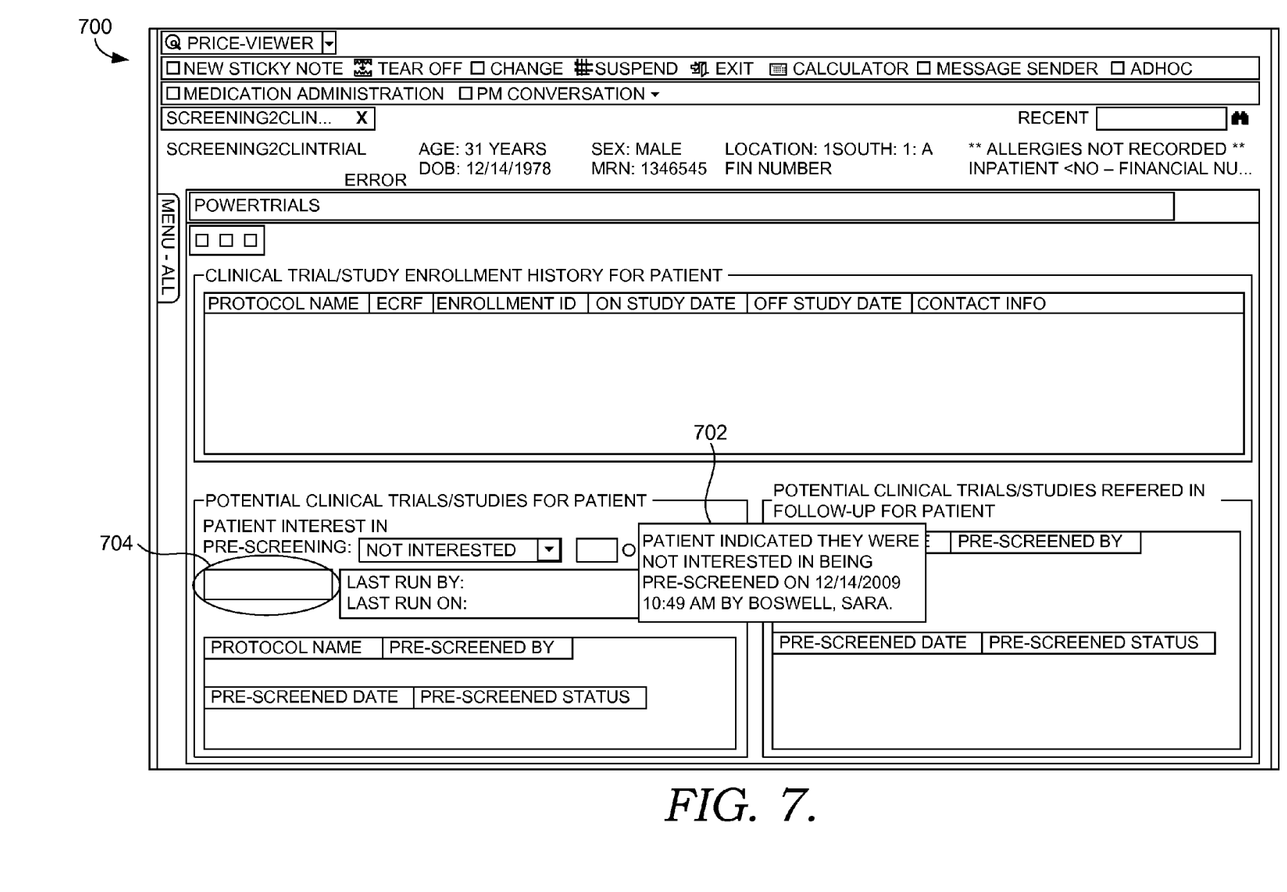
FIG. 7 is a screenshot illustrating yet another exemplary view of information regarding a particular patient's involvement in clinical research, with a default rule of "not available" for pre-screening applied.

FIG. 7 provides another exemplary view 700 of a clinical research activity manager, similar to view 500 of FIG. 5 and view 600 of FIG. 6. In view 700, the default rule of "not available" for pre-screening is in effect. Furthermore, the particular patient record indicates, via a pop-up window 702, that patient has indicated they were not interest in being eligible for pre-screening with respect to protocols that could apply for them. Therefore, because of the explicit instruction from the patient, no option is provided in view 700 for selection of any particular protocols for which the associated patent could be pre-screened and the patient is classified as "screening not eligible".

Figure 8:
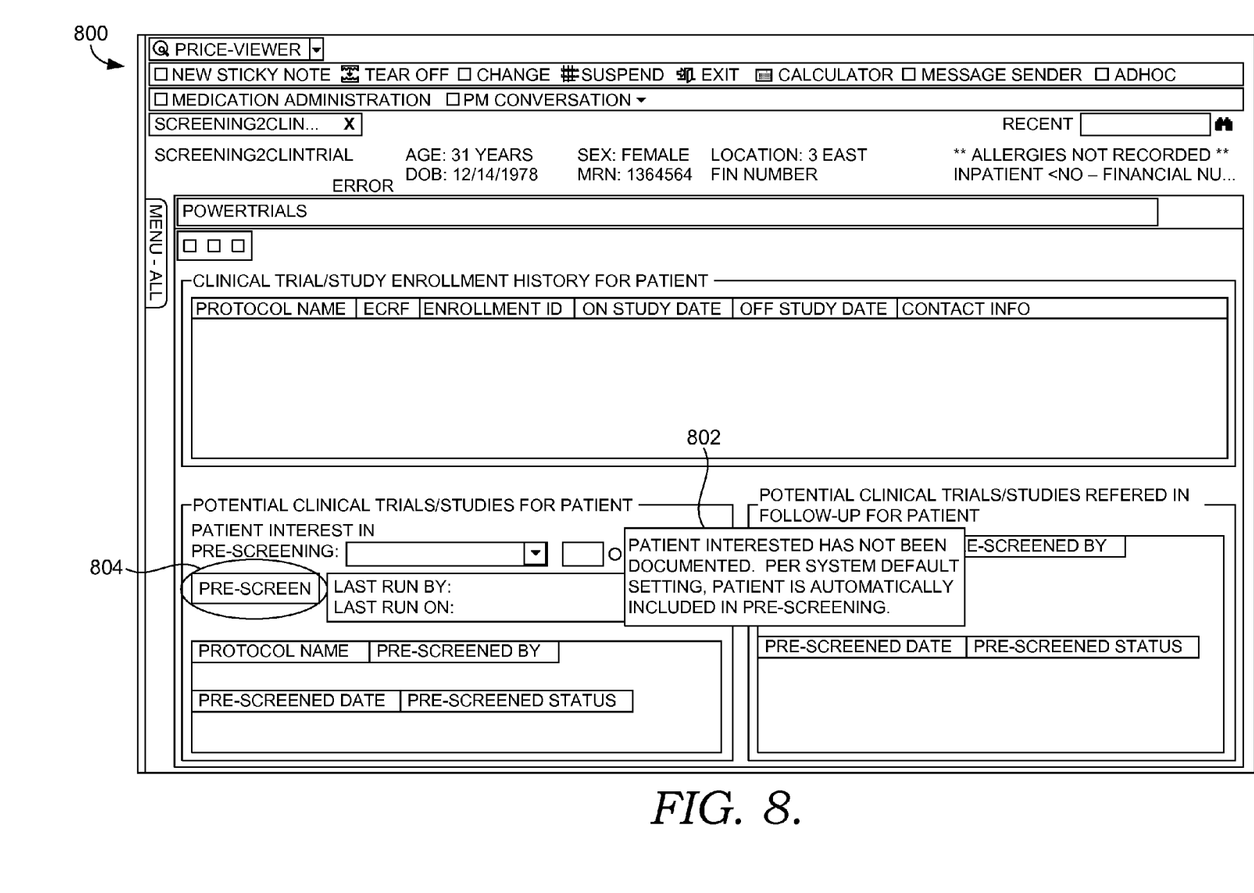
FIG. 8 is a screenshot illustrating an exemplary view of information regarding a particular patient's involvement in clinical research, with a default rule of "available" for pre-screening applied.

With reference to FIG. 8, another exemplary view 800 of a clinical research activity manager is provided. View 800 is similar to the aforementioned views 500, 600 and 700, but is differentiated by the application of the "available rule". Accordingly, the particular patient record shows, via a pop-up window 802, the associated patient has not indicated an interest regarding utilization of their specific health data in evaluating the potential eligibility of the individual for research activities or registries. However, because of the default rule in effect, a pre-screen option 804 is presented and the patient is now classified as "screening eligible". The clinician can select the pre-screen option 804, whereby the patient can be pre-screened to determine if they would qualify for any particular protocols. If alternatively, the patient had confirmed their interest regarding utilization of their specific health data, then optionally, the patient's interest (authorization) could extend to a specific type of research activity or registry, if a protocol (or activity/registry) is available and the specific protocol (or activity/registry) cannot be defaulted to an "available rule". In another alternative scenario, under the application of the "available rule", if a patient confirmed they are not interested, the categorization of "screening not eligible" may extend to either all research activities or registries, or for the specific activity/registry provided in view 800.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer storage media storing
    computer-executable instructions that, when executed by one or more computing devices, cause the one or more computing devices to perform a method for managing the availability of health record data of a pool of individuals, the method comprising:
    establishing one or more default rules regarding accessibility of health data from person-centric health records of the pool of individuals for purposes of evaluating the potential eligibility of such individuals for research activities or registries;
    applying the one or more default rules to categorize individuals of the pool of individuals as pre-screen eligible or pre-screen not eligible;
    prompting each individual to indicate authorization for utilization of their health data in determining the potential eligibility of the individual for research activities or registries;
    for each individual, receiving and storing information in the associated person-centric health record regarding authorization for utilization of their health data in determining the potential eligibility of the individual for research activities or registries; and
    based on the stored authorization information for utilization of their health data in determining the potential eligibility of the individual for research activities or registries, conducting a first update of the categorization of individuals of the pool of individuals as pre-screen eligible or pre-screen not eligible.

2. The media of claim 1, further comprising making accessible the health data from person-centric health records of the individuals in the pre-screen eligible category from the first update of the categorization for purposes of evaluating the potential eligibility of such individuals for research activities or registries.

3. The media of claim 1, wherein the one or more default rules include one of (a) initially listing all individuals of the pool of individuals as pre-screen eligible, or (b) initially listing all individuals of the pool of individuals as pre-screen not eligible.

4. The media of claim 1, further comprising:
   (a) for each individual, receiving and storing information in the associated person-centric health record regarding interest in particular types of research activities or registries; and
   (b) based on (a), extending the categorization of individuals of the pool of individuals as pre-screen eligible or pre-screen not eligible for the particular types of research activities or registries.

5. The media of claim 1, further comprising applying one or more rules associated with a health institution or organization.

6. The media of claim 5, wherein the one or more rules associated with the health institution or organization comprise certain types of diseases or condition that are automatically categorized as pre-screen not eligible.

7. The media of claim 5, further comprising conducting a second update of the categorization of individuals of the pool of individuals as pre-screen eligible or pre-screen not eligible based on the applying one or more rules associated with the health institution or organization.

8. The media of claim 5, further comprising conducting a second update of the categorization of individuals of the pool of individuals as pre-screen eligible or pre-screen not eligible based on the applying one or more rules associated with the health institution or organization.

9. One or more non-transitory computer storage media storing computer-executable instructions that, when executed by one or more computing devices, cause the one or more computing devices to perform a method for managing the availability of health record data of a pool of individuals, the method comprising:
   establishing one or more default rules regarding accessibility of health data from person-centric health records of the pool of individuals for purposes of evaluating the potential eligibility of such individuals for research activities or registries;
   applying the one or more default rules to categorize individuals of the pool of individuals as pre-screen eligible or pre-screen not eligible;
   for each individual, receiving and storing information in the associated person-centric health record regarding authorization for utilization of their health data associated with particular types of research activities or registries; and
   based on the stored authorization information for utilization of their health data associated with particular types of research activities or registries, conducting a first update of the categorization of individuals of the pool of individuals as pre-screen eligible or pre-screen not eligible.

10. The media of claim 9, further comprising applying one or more rules associated with a health institution or organization.

11. The media of claim 10, wherein the one or more rules associated with the health institution or organization comprise certain types of diseases or condition that are automatically categorized as pre-screen not eligible.

12. The media of claim 9, further comprising conducting a second update of the categorization of individuals of the pool of individuals as pre-screen eligible or pre-screen not eligible based on the applying one or more rules associated with the health institution or organization.

13. The media of claim 9, further comprising making accessible the health data from person-centric health records of the individuals in the pre-screen eligible category from the second update of the categorization for purposes of evaluating the potential eligibility of such individuals for research activities or registries.

14. The media of claim 9, wherein the one or more default rules include one of (a) initially listing all individuals of the pool of individuals as pre-screen eligible, or (b) initially listing all individuals of the pool of individuals as pre-screen not eligible.

15. One or more non-transitory computer storage media storing computer-executable instructions that, when executed by one or more computing devices, cause the one or more computing devices to perform a method for managing the availability of health record data of a pool of individuals, the method comprising:
   for each individual, receiving and storing information in the associated person-centric health record regarding authorization for utilization of their health data associated with particular types of research activities or registries;
   applying one or more default rules to categorize individuals of the pool of individuals as pre-screen eligible or pre-screen not eligible; and
   based on the stored authorization information for utilization of their health data associated with particular types of research activities or registries and the applied one or more default rules, conducting a first update of the categorization of individuals of the pool of individuals as pre-screen eligible or pre-screen not eligible.

16. The media of claim 15, further comprising applying one or more rules associated with a health institution or organization.

17. The media of claim 16, wherein the one or more rules associated with the health institution or organization comprise certain types of diseases or condition that are automatically categorized as pre-screen not eligible.

18. The media of claim 15, further comprising conducting a second update of the categorization of individuals of the pool of individuals as pre-screen eligible or pre-screen not eligible based on the applying one or more rules associated with the health institution or organization.

19. The media of claim 15, further comprising making accessible the health data from person-centric health records of the individuals in the pre-screen eligible category from the second update of the categorization for purposes of evaluating the potential eligibility of such individuals for research activities or registries.

20. The media of claim 15, wherein the one or more default rules include one of (a) initially listing all individuals of the pool of individuals as pre-screen eligible, or (b) initially listing all individuals of the pool of individuals as pre-screen not eligible.

* * * * *